United States Patent
Zhang

(10) Patent No.: US 7,238,326 B2
(45) Date of Patent: Jul. 3, 2007

(54) GERMICIDAL TREATMENT SYSTEM WITH STATUS INDICATOR

(75) Inventor: Kanghong Zhang, Long Beach, CA (US)

(73) Assignee: Steril-Aire, Inc., Burbank, CA (US)

( * ) Notice: Subject to any disclaimer, the term of this patent is extended or adjusted under 35 U.S.C. 154(b) by 641 days.

(21) Appl. No.: 10/423,511

(22) Filed: Apr. 24, 2003

(65) Prior Publication Data
US 2004/0213714 A1  Oct. 28, 2004

(51) Int. Cl.
*A61L 2/10* (2006.01)

(52) U.S. Cl. .......... 422/121; 422/119; 315/129; 315/130; 315/135

(58) Field of Classification Search .......... None
See application file for complete search history.

(56) References Cited

U.S. PATENT DOCUMENTS

| | | | |
|---|---|---|---|
| 3,877,152 A * | 4/1975 | Gorman | 34/524 |
| 4,224,553 A | 9/1980 | Hellwig | |
| 4,255,663 A * | 3/1981 | Lewis | 250/436 |
| 4,318,031 A * | 3/1982 | Lonseth et al. | 315/133 |
| 4,353,007 A * | 10/1982 | Moerkens et al. | 315/62 |
| 4,990,313 A | 2/1991 | Pacosz | |
| 5,487,088 A * | 1/1996 | Weltz et al. | 315/276 |
| 5,660,719 A | 8/1997 | Kurtz | |
| 5,742,063 A | 4/1998 | Scroggins | |
| 5,894,130 A | 4/1999 | Bach | |
| 6,053,968 A | 4/2000 | Miller | |
| 6,248,235 B1 | 6/2001 | Scott | |
| 6,261,449 B1 | 7/2001 | Scott | |
| 6,274,049 B1 | 8/2001 | Scott | |
| 6,330,947 B1 | 12/2001 | Scott | |
| 6,464,760 B1 | 10/2002 | Sham | |
| 6,508,367 B2 | 1/2003 | Scott | |
| 6,524,457 B1 | 2/2003 | Scott | |
| 6,818,177 B1 * | 11/2004 | Turcotte | 422/24 |
| 2004/0100208 A1 * | 5/2004 | Readio et al. | 315/291 |

OTHER PUBLICATIONS

Product Catalog for GE Electronic Ballasts, prior art.
Product Catalog for GE Germicidal Lamps, prior art.

* cited by examiner

*Primary Examiner*—E. Leigh McKane
(74) *Attorney, Agent, or Firm*—SoCal IP Law Group LLP; Steven C. Sereboff

(57) ABSTRACT

There is disclosed a germicidal treatment system having a status indicator. The germicidal treatment system comprises at least one mounting assembly attachable to an outside of a wall of an air handling apparatus. Each of the mounting assemblies includes a germicidal lamp and a ballast. The germicidal lamp is coupled to the ballast. The germicidal treatment system includes a power cord to receive electrical power and to provide electrical power to the ballast. A status indicator to indicate the functioning status of the germicidal treatment system.

11 Claims, 5 Drawing Sheets

GERMICIDAL TREATMENT SYSTEM WITH STATUS INDICATOR

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure as it appears in the Patent and Trademark Office patent files or records, but otherwise reserves all copyright and trade dress rights whatsoever.

BACKGROUND OF THE INVENTION

1. Field of the Invention

The invention relates to germicidal treatment systems that include germicidal lamps.

2. Description of Related Art

Heating, ventilation and air conditioning (HVAC) units may be augmented with germicidal treatment systems that emit ultraviolet light to eradicate harmful microorganisms in the air, in ducts and on and in HVAC units. Typical germicidal treatment systems comprise a lamp and a fixture. The fixture typically includes an electronic or magnetic ballast.

The fixture of a germicidal treatment system may be attached to an outside of a wall of HVAC units and ducts such that the lamp portion of the germicidal treatment system that emits ultraviolet light is on the inside of the HVAC unit or duct. As such, when the lamp emits ultraviolet light, the light is emitted within the HVAC unit and duct. In this way, the ultraviolet light is contained within the HVAC unit and ducts and is not noticeable by persons on the outside of the units and ducts.

DESCRIPTION OF THE DRAWINGS

The invention will be described by way of exemplary embodiments, but not limitations, illustrated in the accompanying drawings in which like references denote similar elements.

FIG. 6 is a block diagram of the components of a second status indicator circuit.

DETAILED DESCRIPTION OF THE INVENTION

Throughout this description, the embodiments and examples shown should be considered as exemplars, rather than limitations on the apparatus and methods of the invention.

As used herein, the term air handling apparatus includes air carrying ducts and air treating units, such as heating, ventilation and air conditioning (HVAC) units of all kinds including, but not limited to, air conditioners, heaters, humidifiers, and dehumidifiers, whether installed as a single unit, as multiple units and in combination, as well as any air treatment or air delivery device and associated ducts.

Figure 1:
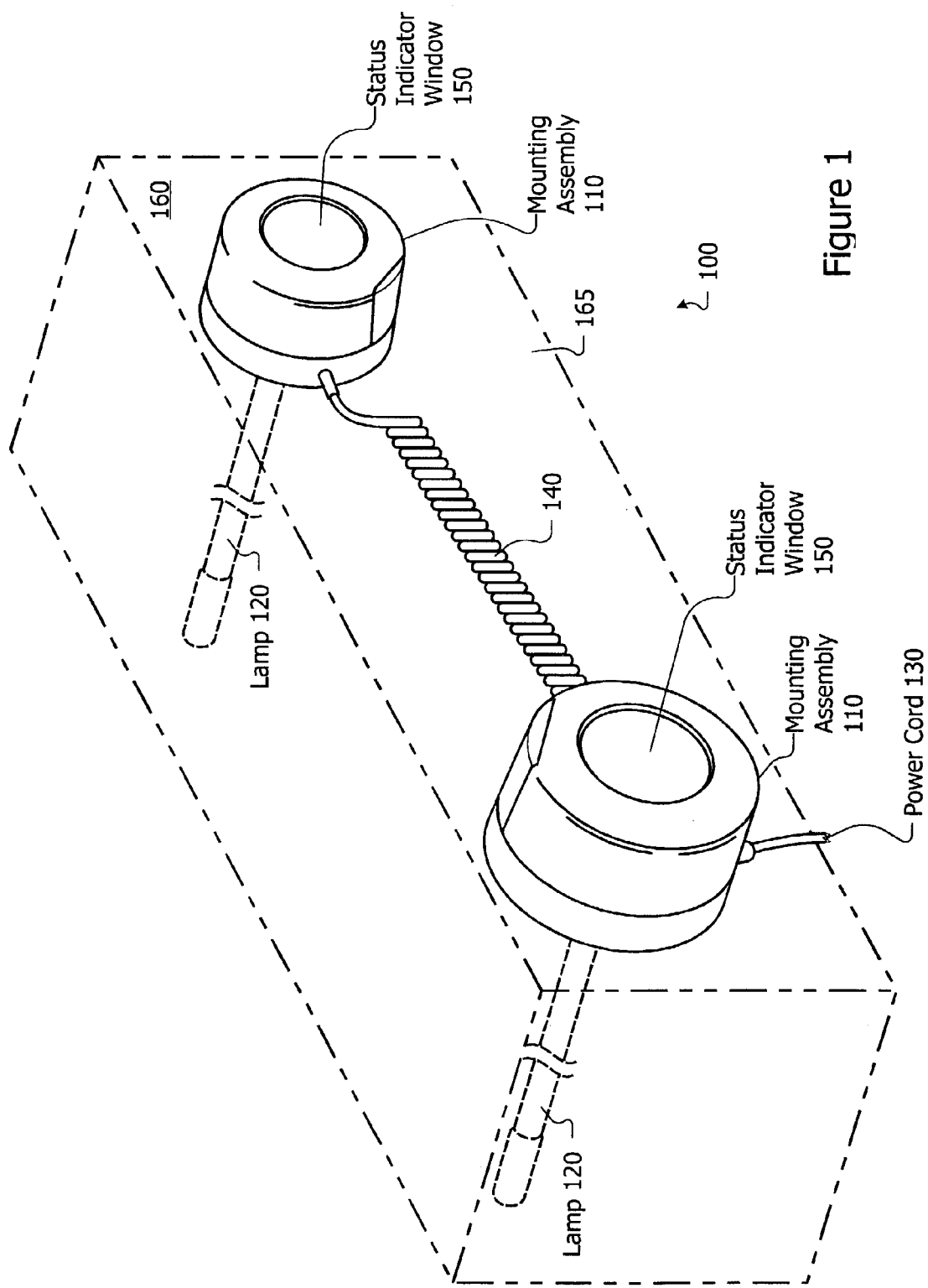
FIG. 1 is a top perspective view of a dual-lamp germicidal treatment system attached to a wall of an air handling apparatus.

FIG. 1 is a top perspective view of a dual-lamp germicidal treatment system 100 attached to a wall 160. The wall 160 may be a duct wall of an air handling apparatus. As shown, the mounting assemblies 110 are generally circular in shape and are coupled together with extensible cord 140. The germicidal treatment system 100 receives electrical power from power cord 130. The mounting assemblies 110 include a receiver to receive an end of germicidal lamp 120. The receiver may be a socket. A ballast (not shown) may be included in the mounting assembly 110 or integrated with germicidal lamp 120.

When the germicidal treatment system 100 is installed, the mounting assemblies 110 are attached on an outside surface 164 of the wall 160. The germicidal lamps 120 pass through a hole in the wall 160 from the inside of the wall 160 through the wall 160. The germicidal lamps 120 are coupled to the receivers of the mounting assemblies 110 on the outside of the wall 160. In this embodiment, the receiving holes have a diameter sufficient to accommodate the germicidal lamps 120.

In other embodiments, the extensible coiled cord 140 may be replaced with any coupling apparatus that allows the mounting assemblies to be adjusted, such as for example, arms with hinges, accordion portions, telescoping portions, interlocking portions, and others.

The mounting assemblies 110 of the germicidal treatment system 100 may be attached to the wall of an air handling apparatus using screws, bolts, rivets, glue, and other fasteners. In other embodiments, hook and loop fasteners such as Velcro® brand hook and loop fasteners may be used to attach the germicidal treatment system to the wall of an air handling apparatus.

When a germicidal treatment system 100 is attached as shown in FIG. 1 on the outside surface 165 of a wall 160 of an air handling apparatus, the germicidal lamp 120 emits ultraviolet light on the inside of the wall 160 of the air handling apparatus. The germicidal lamp 120 emits ultraviolet light to treat the air located in, the interior surfaces of, and the internal components of the air handling apparatus. As the germicidal lamp emits ultraviolet light internal to the air handling apparatus, the ultraviolet light is typically not noticeable by persons located on the outside of or external to the air handling apparatus.

So that users of the germicidal treatment system 100 may easily learn when a germicidal lamp 120 is failing or is out, a status indicator window is included in mounting assembly 110. The status indicator window 150 illuminates when the germicidal lamp 120 is functioning normally. The status indicator window 150 becomes dark when the germicidal lamp 120 is not functioning normally. In one embodiment, a logo, brand name, icon, text, and/or graphic may be included on the surface of status indicator window 150. In this way, when the germicidal lamp 120 is functioning normally, the logo, brand name, icon, text, and/or graphic lights up. The status indicator window 150 may be generally round, rectangular or any other shape.

In another embodiment, the status indicator window 150 may also illuminate when the ballast is functioning normally and become dark when the ballast is not functioning normally.

Figure 2:
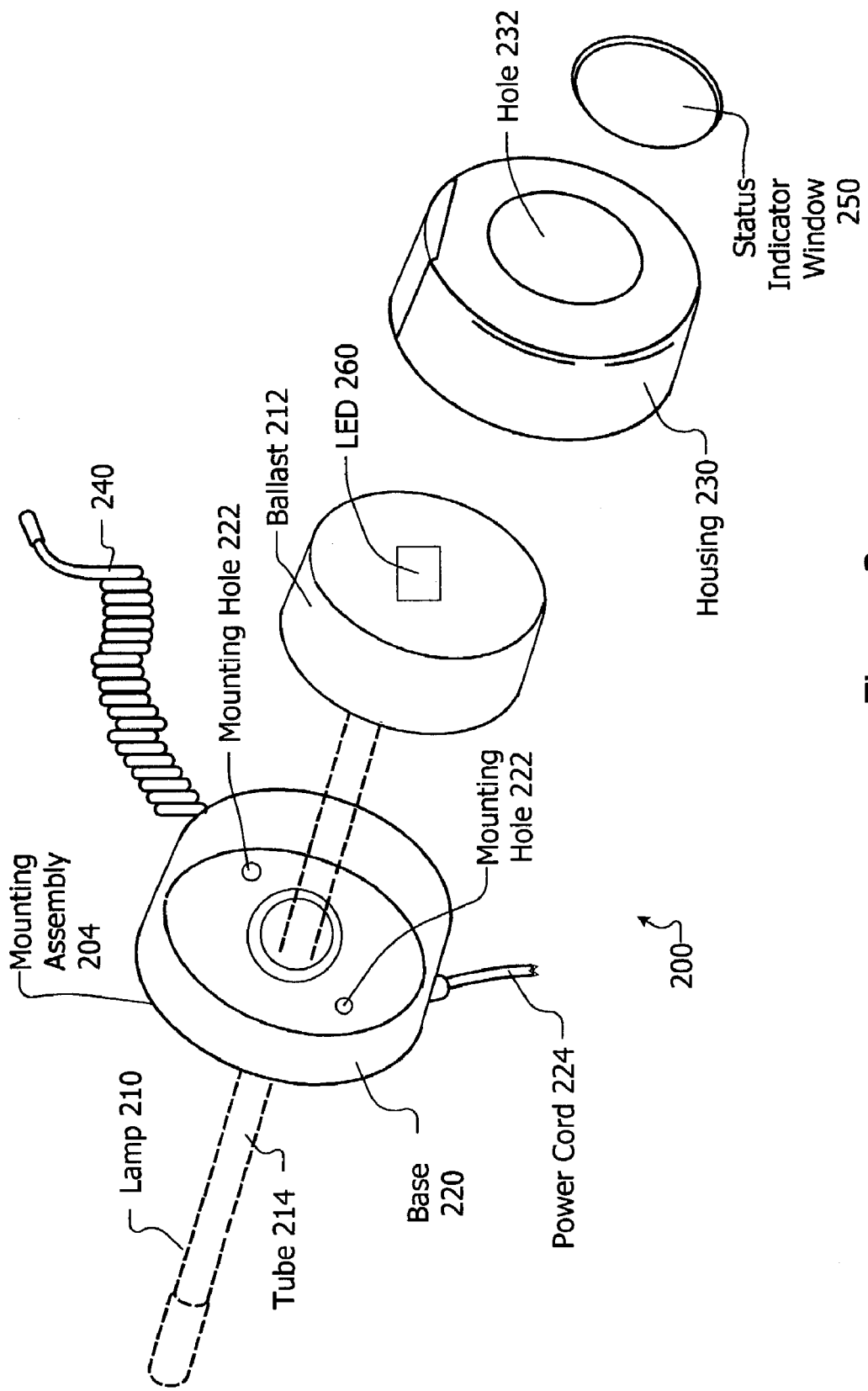
FIG. 2 is a partially exploded perspective view of a germicidal treatment system having a status indicator.

FIG. 2 is a partially exploded perspective view of a germicidal treatment system 200 having a status indicator. In this embodiment, germicidal treatment system 200 includes at least one mounting assembly 204. Each mounting assembly 204 includes a germicidal lamp 210. When the germicidal treatment system 200 includes more than one mounting assembly 204, the mounting assemblies may be adjustably coupled together with a extensible coiled cord 240, or may be coupled in any other manner.

Mounting assembly 204 is comprised of a base 220 through which one end of a germicidal lamp 210 passes. In various embodiments, ballast 212 is incorporated with or is separate from germicidal lamp 210. Ballast 212 is enclosed or encapsulated between base 220 and housing 230. That is, ballast 212 is located between base 220 and housing 230. The housing 230 and base 220 may have corresponding receivers and connectors or other coordinated attaching elements to allow for easy attachment and removal of housing 230, such as, for example, by snapping on and off. The removal of housing 230 allows for access to the germicidal lamp 210 so that the germicidal lamp 210 may be replaced when it is not functioning normally.

Base 220 may be coupled to a wall or housing of an air handling apparatus, as shown, for example, in FIG. 1. This coupling may be made using bolts, screws, rivets or other fastening systems placed through mounting holes 222. Although two mounting holes 222 are shown, one or more mounting holes may be included in base 220. Base 220 also includes power cord 224 which is coupled to an electrical power source.

In one embodiment, the germicidal lamp 210 may be an integrated germicidal lamp that includes a ballast 212 and a tube 214. In another embodiment, the germicidal lamp 210 may solely be comprised of a tube 214. The tube 214 may have a T5, T8, or other diameter.

In one embodiment, the germicidal lamp 210 is single ended. Single tube and multiple tube single ended germicidal lamps as well as u-shaped, j-shaped and other shaped single ended germicidal lamps may be incorporated in the germicidal treatment systems described herein. In other embodiments, the germicidal lamps may be double ended. The germicidal lamps 210 may have any appropriate shape, length and diameter.

The germicidal lamps 210 may be ultraviolet (UV) germicidal lamps that emit sufficient UV-C radiation to eradicate airborne germs and germs that accumulate in the air in and on the internal surfaces of air handling apparatus. In one embodiment, the germicidal lamps 210 emit broadband UV-C in the range of 250–260 nm.

The ballast 212 may be any electrical or magnetic ballast sufficient to control the electrical power necessary to illuminate germicidal lamp 210. In one embodiment, ballast 212 is generally round. In various embodiments, ballast 212 may have generally the same diameter as the diameter of tube 214, may have a diameter greater than that of tube 214, or may have a diameter smaller than the diameter of tube 214. In other embodiments, the ballast 212 is not round and may be any shape.

In one embodiment, at least one light emitting device such as light emitting diode 260 is included in mounting assembly 204. As used herein, LED refers to both any light emitting device as well as a light emitting diode. The LED 260 may be incorporated with or otherwise coupled to the ballast 212. Although shown physically on "top" of ballast 212, in one embodiment, the LED 260 is positioned electrically between the ballast 212 and the germicidal lamp 210. The LED 260 may be physically positioned between the ballast 212 and the germicidal lamp 210. The LED 260 may be any device that emits light.

When the germicidal lamp 210 is functioning properly, the light emitting device illuminates to emit light through status indicator window 250. The status indicator window 250 may be made from a translucent, semi-opaque, semi-transparent plastic or other material that illuminates, glows, or fluoresces when LED 260 emits light. In another embodiment, the status indicator window 250 may be made from a transparent or clear material. The status indicator window 250 snaps in or is otherwise attached to the hole 232 of housing 230. In one embodiment, the combination of the LED 260 and status indicator window 250 serve to indicate the functioning status of the germicidal lamp 210. In another embodiment, the combination of the LED 260 and status indicator window 250 serve to indicate the functioning status of the germicidal lamp 210 and the ballast 212.

In one embodiment, there is no status indicator window 250 and no hole 232. In this embodiment, the LED 260 protrudes from an opening in the housing 230. In a related embodiment, the LED 260 is located behind the housing 230 such that it is internal to the mounting assembly 204, and either the entire housing 230 or an outer or facing portion of the housing 230 is made of a translucent plastic or other material through which light from the LED 260 may be perceived. In yet another embodiment, light from an LED located behind the housing 230 may be channeled through a light pipe from the LED either to or through the housing 230.

The base 220 and housing 230 of mounting assembly 204 may be manufactured from any resilient, strong, durable material that is impervious to temperature changes, such as, for example, but not limited to, metals, plastics, and resins. In some embodiments, the exterior of mounting assemblies 204 is impervious to water so that the contents of the mounting assembly 204 remain dry. The mounting assembly 204 may be any shape such as rectangular, square, circular, etc.

Figure 3:
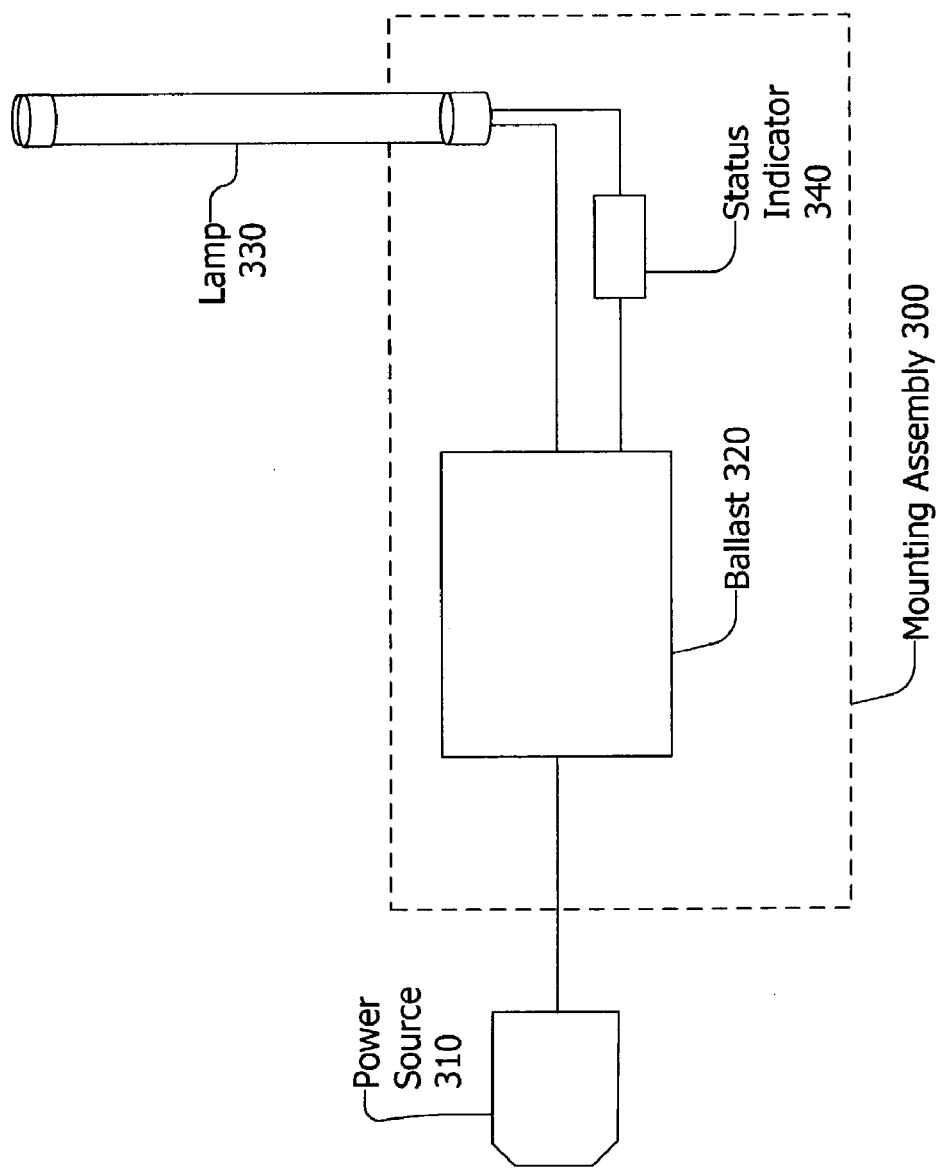
FIG. 3 is a block diagram of the components of a germicidal treatment system having a status indicator.

FIG. 3 is a block diagram of the components of a germicidal treatment system having a status indicator 340 to indicate the status of the germicidal lamp 330. In one embodiment, power source 310 provides power to the mounting assembly 300. Ballast 320 is coupled to and receives electrical power from the power source 310. Lamp 330 is coupled to and receives power from the ballast 320. The status indicator 340 may be positioned between ballast 320 and germicidal lamp 330. In various embodiments, the status indicator 340 illuminate, dims or changes color to signify that the germicidal lamp 330 and/or the ballast 320 are in working order.

When a germicidal lamp is in working order, the germicidal lamp 330 uses, draws or pulls an amount of current from the ballast 320. In one embodiment, the germicidal lamp 330 draws current in the range of 400–450 mA. The current drawn by the germicidal lamp 330 may be referred to as the power or current required to illuminate the germicidal lamp.

The status indicator 340 illuminates when the current received over line 332 from germicidal lamp 330 exceeds a threshold, which may be referred to as the current threshold. The current threshold may be, for example, without limitation, in the range of from 200 mA to 400 mA. In one embodiment, the current threshold is 250 mA. The status indicator 340 ceases to illuminate when the current received over line 332 is less than or equal to the current threshold. In one embodiment, the status indicator 340 dims as the current received over line 332 diminishes until the current threshold is reached, at which time the status indicator 340 ceases to illuminate.

The current threshold of the status indicator 340 may be based on the power required of the germicidal lamp 330. Generally, the current threshold is based on but is a value smaller then the power required of the germicidal lamp 330.

As in the prior two paragraphs, when the power required of a germicidal lamp is of 400–450 mA, the current threshold may be in the range of 200 to 400 mA, and may be 250 mA. In another example, when the power required of a germicidal lamp is of 600–650 mA, the current threshold may be in the range of 400 to 600 mA, and may be 500 mA. These are only examples. The power required of the germicidal lamp and the current threshold may be any values that correspond to and are based on the particular germicidal lamp.

When a germicidal lamp is in working order, the germicidal lamp 330 serves as a resistor such that the resistance of the germicidal lamp is lower when the germicidal lamp 330 is in regular working order, and is higher when the germicidal lamp 330 is not in proper working order. Examples of when a germicidal lamp is not in working order and its current draw and its resistance increases include: when the germicidal lamp deteriorates such that its electrical properties change; when the filament in the germicidal lamp burns out or deteriorates; when the tube of the germicidal lamp leaks; and others.

In one embodiment, the status indicator 340 illuminates when the resistance in the germicidal lamp 330 sensed over line 332 is below a threshold, which may be referred to as the resistance threshold. That is, the status indicator 340 ceases to illuminate when the resistance measured in the germicidal lamp is greater than or equal to the resistance threshold. In one embodiment, the status indicator 340 dims as the resistance of the germicidal lamp 330 increases until the resistance threshold is reached, at which time the status indicator 340 ceases to illuminate.

Figure 4:
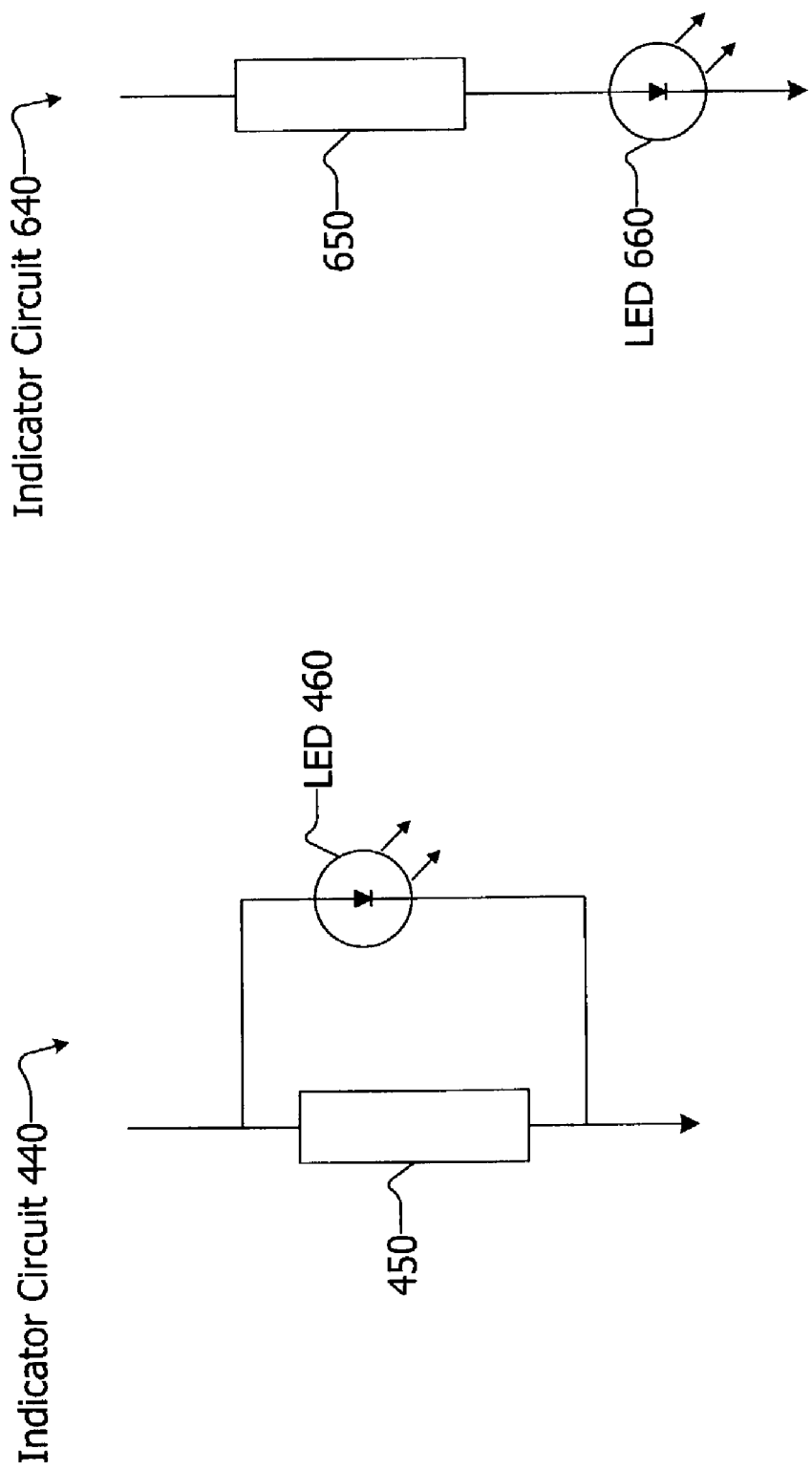
FIG. 4 is a block diagram of the components of a status indicator circuit.

FIG. 4 is a block diagram of the components of a status indicator circuit 440. Status indicator circuit 440 may be included in the mounting assembly 300 of FIG. 3 as status indicator 340. As shown in FIG. 4, status indicator circuit 440 includes a component 450 which adds impedance to the circuit. Component 450 may be a capacitor, a resistor, an inductor or other electrical device. Component 450 is in parallel with light emitting diode 460. In this way, component 450 passes current from the germicidal lamp sufficient to drive the light emitting diode 460. In one embodiment, the light emitting diode requires about 5 mA of current to illuminate. Current from the germicidal lamp passes through component 450. The resulting voltage across component 450 illuminates light emitting diode 460. When the current from the germicidal lamp drops, the voltage across component 450 will drop. Less current will be available for the light emitting diode 460. This causes the light emitting diode 460 to dim until the current threshold in the indicator circuit 400 is reached. When the current threshold is reached, the light emitting diode 460 ceases to emit light.

Figure 5:
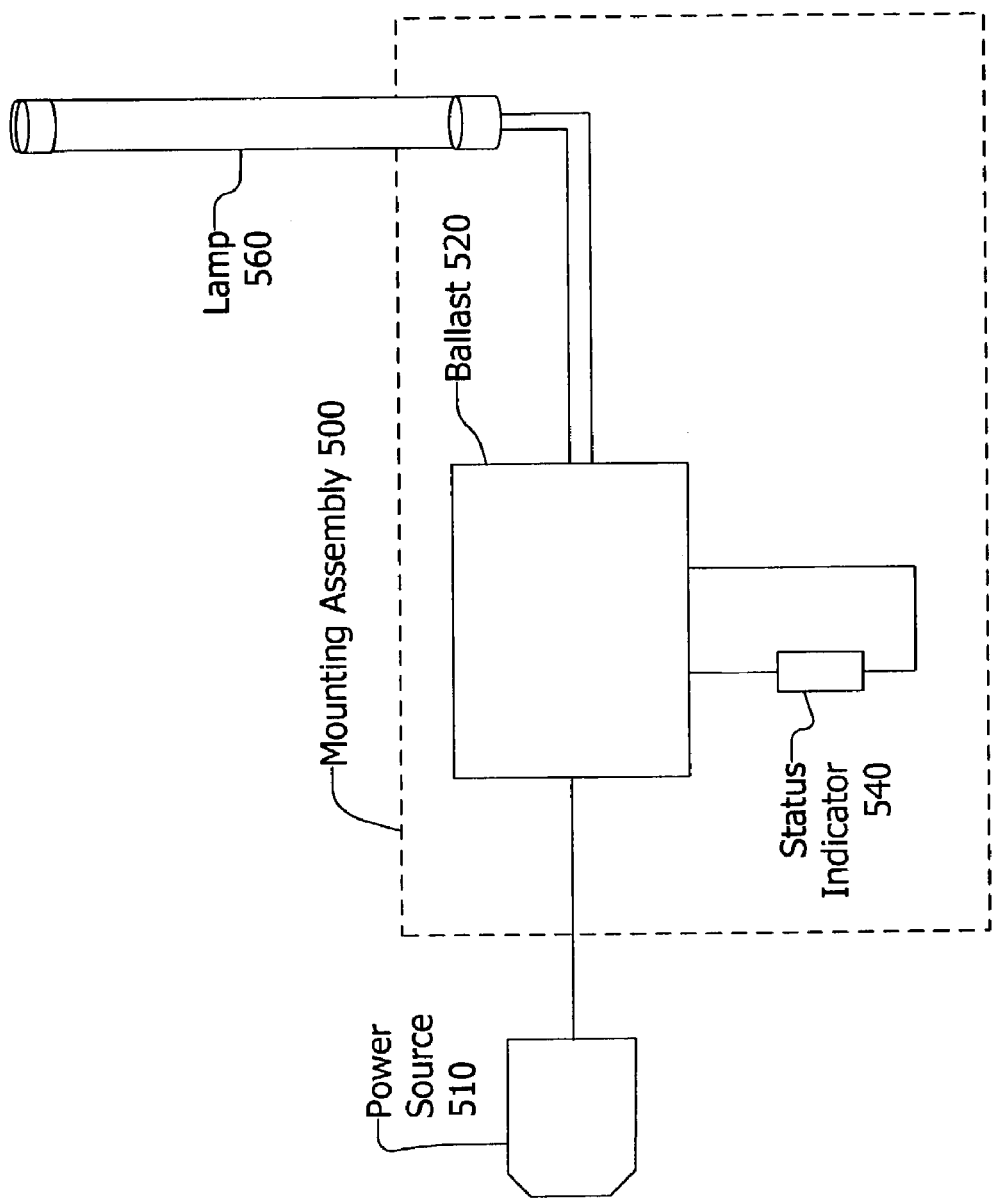
FIG. 5 is a block diagram of the components of a second germicidal treatment system having a status indicator.

FIG. 5 is a block diagram of the components of a second germicidal treatment system having a status indicator. In one embodiment, power source 510 provides power to the mounting assembly 500. Ballast 520 is coupled to and receives electrical power from the power source 510. Germicidal lamp 560 is coupled to and receives power from the ballast 520. In this embodiment, the status indicator 540 is coupled to the ballast 520. The status indicator 540 may stop illuminating, dim, or change color when the ballast 520 is not functioning properly.

The status indicator 540 may illuminate when the efficiency of the ballast 520 is less than a certain threshold and/or when the oscillation of the current drawn by the ballast 520 is outside an acceptable range. When the ballast 520 is not functioning properly, the ballast 520 stops oscillating. When the oscillation ceases, there is no voltage source for the status indicator 540. When the voltage drops, the status indicator 540 dims, stops illuminating or changes color, depending on the embodiment.

FIG. 6 is a block diagram of the components of a second status indicator circuit 640. Status indicator circuit 640 may be included in the mounting assembly 500 of FIG. 5 as status indicator 540. As shown in FIG. 6, status indicator circuit 640 includes a component 650 which adds impedance to the circuit. Component 650 may be a capacitor, a resistor, an inductor or other electrical device. Component 650 is in series with light emitting diode 660. In one embodiment, the status indicator circuit 640 does not sense the current drawn by a germicidal lamp, but senses the current oscillation of the ballast and/or the circuit that includes the ballast and the germicidal lamp. The component 550 limits the current to 5 mA so the LED can function properly.

In one embodiment, a monitoring unit may be included in status indicators 340 and/or 540. The monitoring unit may control whether the status indicators 340 and 540 illuminate based on at least one of the resistance, current, efficiency and oscillation measured regarding germicidal lamp 330 and/or ballast 520.

In another embodiment, at least two LEDs may be incorporated in the status indicators 340 and/or 540. In this embodiment, a first LED may illuminate a first color (such as, for example, green) when the germicidal lamp 330 is working properly, and a second LED may illuminate a second color (such as, for example, red) when the ballast 520 is functioning properly. The second LED may illuminate based on at least one of the current, resistance, efficiency and oscillation from the ballast 520.

In another embodiment, one or more three way LEDs may be used in the status indicators 340 and/or 540. One LED may illuminate a first color, such as, for example, green, when the germicidal lamp is functioning properly; may illuminate a second color, such as, for example, yellow or red, when the germicidal lamp is not functioning properly; and may cease to illuminate when the germicidal lamp has ceased to function. A second LED may operate similarly with respect to the functioning of the ballast.

In yet another embodiment, the status indicator windows 150 and 250 may be replaced with a liquid crystal display (LCD) or other display. A monitoring unit may be coupled between the ballast and the germicidal lamp to evaluate whether the germicidal lamp is functioning properly. The monitoring unit is coupled to the display and controls what is shown on the display. The display may include a short text description of the condition of the germicidal lamp in the germicidal treatment system. For example, the display may show the letters "OK" when the germicidal lamp is functioning normally, may display the word "CHECK", when the germicidal lamp is not functioning properly, and may display the work "REPLACE" when the germicidal lamp has ceased to function. Similarly, the monitoring unit may cause the display to scroll information about the state of the germicidal lamp and/or the state of the electrical circuit that includes the germicidal lamp. The scrolling information may include data such as resistance, current, oscillation, efficiency, and other data, as well as status words or phrases such as, for example, "LAMP IS OK," "CHECK LAMP," and "REPLACE LAMP."

In another embodiment, the status indicator may include a sound emitting device. In this embodiment, a monitoring unit is electrically coupled between the germicidal lamp and the ballast. The monitoring unit may cause the sound emitting device to emit sounds when the germicidal lamp and/or the electrical circuit that includes the germicidal lamp is not functioning properly. In one embodiment, the sound emitted may be akin to an alarm or other attention grabbing sound, such as, for example, a buzz, chime, and others. In another embodiment, the sound emitted may be synthesized speech that alerts the user to "CHECK LAMP" or "REPLACE LAMP" when appropriate. The sound emitted or speech synthesized may be based on the monitoring unit evaluating, as set forth in more detail above, the resistance, current, oscillation, and/or the efficiency of the germicidal lamp and/or the electrical circuit that includes the germicidal lamp. In one embodiment, the status indicator may include a sounded emitting device paired with a light emitting device and/or a display that are controlled by a monitoring unit.

Although exemplary embodiments of the invention have been shown and described, it will be apparent to those having ordinary skill in the art that a number of changes, modifications, or alterations to the invention as described herein may be made, none of which depart from the spirit of the invention. All such changes, modifications and alterations should therefore be seen as within the scope of the invention.

It is claimed:

1. A germicidal treatment system comprising:
   a mounting assembly attachable to an outside of a wall of an air handling apparatus
   a germicidal lamp coupled to a ballast, the ballast located within the mounting assembly
   a power cord to receive electrical power, the power cord to provide electrical power to the ballast
   a light emitting device (LED) electrically coupled between the germicidal lamp and the ballast to illuminate when the germicidal lamp is functioning properly
   wherein the LED illuminates when current from the ballast oscillates outside an acceptable oscillating range.

2. A germicidal treatment system comprising:
   a mounting assembly attachable to an outside of a wall of an air handling apparatus
   a germicidal lamp coupled to a ballast, the ballast positioned in the mounting assembly
   a power cord to receive electrical power, the power cord to provide electrical power to the ballast
   a status indicator electrically coupled between the germicidal lamp and the ballast to indicate a functioning status of the germicidal treatment system
   wherein the status indicator illuminates when current from the ballast oscillates outside an acceptable oscillating range.

3. The germicidal treatment system of claim 2 wherein the status indicator comprises
   a monitoring unit coupled to a liquid crystal display (LCD), the monitoring unit to display a text message on the LCD indicating the functioning status.

4. The germicidal treatment system of claim 2 wherein the status indicator comprises
   a light emitting device (LED) to illuminate to indicate the functioning status.

5. The germicidal treatment system of claim 2 wherein the status indicator comprises
   a monitoring unit coupled to a light emitting device (LED) the monitoring unit to cause the LED to illuminate to indicate the functioning status.

6. The germicidal treatment system of claim 2 wherein the functioning status is evaluated based on at least one of an electrical current drawn by the germicidal lamp, a resistance of the germicidal lamp, and an efficiency of the electrical circuit that includes the germicidal lamp.

7. The germicidal treatment system of claim 2 wherein the germicidal lamp and the ballast are integrated as a single unit.

8. The germicidal treatment system of claim 2 wherein the germicidal lamp, the status indicator and the ballast are integrated as a single unit.

9. The germicidal treatment system of claim 2 further comprising an indicator window disposed proximate the status indicator, wherein when the status indicator illuminates, a text or a graphic becomes visible.

10. The germicidal treatment system of claim 2 further comprising a sound emitting device which emits a sound when the status indicator illuminates.

11. An air handling apparatus having the germicidal treatment system of claim 2 attached thereto.

* * * * *